United States Patent [19]
Gilby

[11] Patent Number: 5,153,679
[45] Date of Patent: Oct. 6, 1992

[54] APPARATUS AND PROCESS FOR MEASURING LIGHT ABSORBANCE OR FLUORESCENCE IN LIQUID SAMPLES

[75] Inventor: Anthony C. Gilby, Foxborough, Mass.

[73] Assignee: Millipore Corporation, Bedford, Mass.

[21] Appl. No.: 733,545

[22] Filed: Jul. 22, 1991

Related U.S. Application Data

[63] Continuation-in-part of Ser. No. 414,839, Sep. 29, 1989, abandoned.

[51] Int. Cl.[5] ............................................. G01N 21/85
[52] U.S. Cl. .................................... 356/440; 356/328; 356/410
[58] Field of Search ............... 356/246, 440, 410, 411, 356/328

[56] References Cited

U.S. PATENT DOCUMENTS

| | | | |
|---|---|---|---|
| 3,614,242 | 10/1971 | Hrdina | 356/246 X |
| 4,011,451 | 3/1977 | Nelson | 356/246 X |
| 4,014,612 | 3/1977 | Atwood et al. | 356/325 |
| 4,475,813 | 10/1984 | Munk | 356/410 X |
| 4,822,168 | 4/1989 | Nogami et al. | 356/411 X |

FOREIGN PATENT DOCUMENTS 61-105445  5/1986  Japan ..................................... 356/246

Primary Examiner—Vincent P. McGraw
Attorney, Agent, or Firm—Andrew T. Karnakis; Paul J. Cook

[57] ABSTRACT

An apparatus for measuring light absorbance in a liquid sample which includes a light source for directing light into a sample cell, a cylindrical sample cell, a light detector for measuring intensity of light emitted from the cell and focussing means for forming a tapered light beam to pass through the sample cell. The tapered light beam can be either a diverging beam or a converging beam through the cell. When the light beam is a diverging beam, a masking means is positioned downstream of the cell to assure that any light striking the cell wall is not directed to the light detector.

5 Claims, 4 Drawing Sheets

APPARATUS AND PROCESS FOR MEASURING LIGHT ABSORBANCE OR FLUORESCENCE IN LIQUID SAMPLES

REFERENCE TO RELATED APPLICATION

This application is a continuation-in-part of copending application Ser. No. 07/414,839, filed Sept. 29, 1989, now abandoned.

BACKGROUND OF THE INVENTION

This invention relates to a photometric apparatus useful in liquid chromatography and, more particularly to such an apparatus which utilizes a sample cell and associated optic means which prevents light rays from impinging on the cell walls or prevents such impinged rays from impinging on downstream detection means.

In a liquid chromatography system, detection of sample constituents is effected by passing the eluent from a liquid chromatography column through a small volume sample cell, passing light through the sample cell and detecting the light emitted from the cell to determine characteristic light absorbance by the sample. It is known that substantial spurious radiation signals are generated by differences in refractive index of the sample and solvents flowing through the cell. These index differences produce complex lens-like effects which can cause a variable proportion of the rays passing through a small photometer cell to impinge on the walls. Since rays which encounter the cell walls are partially absorbed, refractive index variations cause the instrument baseline to be unstable, and sample absorbance values to be in error.

The size and shape of an absorption cell for a high performance liquid chromatograph (HPLC) UV-Visible detector is a compromise between the following three factors. First, it is important to pass a high light flux through the cell to achieve a high signal-to-noise-ratio measurement. Second, the cell volume must be kept low to prevent peak spreading and loss of chromatographic resolution. Third, for a given cell volume and optical throughput, the cell pathlength should be as long as possible to maximize sample absorption. These factors lead to the typical dimensions of a conventional HPLC-UV-Vis absorption flow cell; 10 mm long, 1 mm diameter and about 8 micro liters volume. In processes wherein samples are caused to fluoresce and the amount of fluorescence is measured, light rays striking the cell walls also is a problem. This is due to the fact that there is some adsorbance of previously analyzed samples by the transparent cell walls which fluoresces when exposed to light rays and thereby causes spurious signals.

It has been proposed in U.S. Pat. Nos. 4,011,451 and 4,276,475 to provide a flow-cell whereby the lens effect is rapidly dissipated by a progressive increase in the cross-sectional area of the flow-cell along the flow-path. The wall of the flow-cell forms a diverging surface of rotation whereby the walls form an angle of divergence of several degrees with the axis of the cell. The optical system avoids any substantial radiation from entering the cell at sharp angles which could result in the radiation impinging on the walls of the cell. The divergence of the cell walls substantially dissipates the undesirable effect of the refractive index gradients encountered in HPLC separations. Angles of divergence between the axis of the flowpath and the wall of the cell of 1° to 3° are disclosed to be most advantageous.

While the tapered or conically shaped cells described in these two patents provides substantial advantages over the prior art, they have some disadvantages which would desirably be overcome. The required cell volume is undesirably increased as compared to a cylindrically shaped cell. Increased sample cell volume causes band spreading of the light passing through the sample cell. In addition, a conically shaped cell is more difficult to produce and therefore is more expensive than a cylindrically shaped cell having a constant circular cross-section. Therefore, it would be desirable to provide a means to effect liquid chromatography which permits minimizing sample cell volume and which avoids the need for a non-cylindrically shaped sample cell, while still preserving high optical throughput and insensitivity to refractive index changes.

SUMMARY OF THE INVENTION

The present invention is based on the discovery that by controlling the shape of the light beam passing through a sample cell, a cylindrically shaped sample cell having a constant circular cross-section can be employed while preventing any light striking the walls of the cell from impinging on a downstream photodetector. In this invention lenses are positioned prior to the entrance of the sample cell and/or after the exit of the sample cell. The lens or lenses form a tapered light beam passing through the cell. The tapered light beam converges toward the cell exit in one embodiment referred to herein as the "taper beam cell". In a second embodiment the cell is flooded with light, but the portion of the beam selected by the optical system diverges to just fill the cell at the exit end of the cell. Any portion of the light striking the cell walls is masked to prevent its impingement on a downstream photodetector. The second embodiment is referred to herein as the "reverse taper beam cell".

DESCRIPTION OF SPECIFIC EMBODIMENTS

Figure 1:
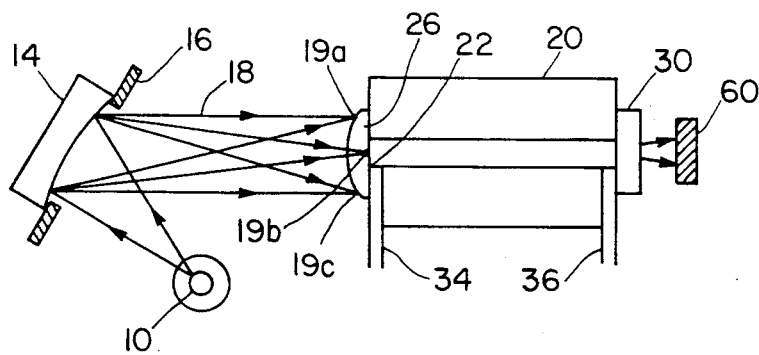
FIG. 1 is a schematic view of an apparatus employing the taper beam cell of this invention.

The purpose of this invention is achieved when utilizing either the taper beam cell or the reverse taper beam cell. That is, light passing through a sample cell to be subsequently analyzed either does not impinge upon the cell wall (taper beam cell) or light fills the cell, but rays impinging on the cell walls are masked prior to striking the detector, (reverse taper beam cell).

In the taper beam cell embodiment, light from the central, hot-spot of a lamp such as a deuterium lamp, a tungsten halogen lamp or the like is focussed on the entrance of the cell so as to overfill the entrance of its cylindrical bore. A nominal magnification such as 2X or 3X is desirable. This ensures that light from the brightest part of the light source encompasses the desired portion of the area at the entrance of the cell, and that the source image will have a reasonably large depth of field near the cell entrance. The angular range of rays collected is well within the central maximum of the source. The light rays converge from the first focussing means to form an image of the source at the cell entrance. The cell entrance is the primary field stop of the system. The primary aperture stop is located near the first focussing means to define the shape of the light beam entering the cell. The first focussing means can be a lens, mirror or grating which may carry a mask to properly establish the aperture.

In the taper beam cell embodiment, the focussed light beam enters the cell through a first lens chosen to form an image of the primary aperture step near the exit window of the cell, when the cell is filled with liquid sample. The size of this image is smaller than the internal diameter of the cell so that, at the cell exit there is established a clearance between the inner diameter of the cell and the outer fringe of the beam which increases towards the cell exit. The clearance is designed to allow refractive index gradients, of the magnitude normally encountered in HPLC to bend the rays without the rays impinging the cell walls. The first lens preferably is sealed to the cell entrance in place of the normally flat window. A detector may be located directly after the cell to intercept all of the rays leaving the cell, or additional optics including a lensed exit window of the cell may be employed, to transfer light to the detectors.

The embodiment just described is a taper beam cell with the field stop of the optical system located at the entrance of the cell. This is an ideal arrangement when the cell is located, for example, after a wave-length-selecting grating spectrometer and the cell entrance aperature becomes the spectrometer exit slit. However, if it is desired to build an absorbance detector based on a photodiode array spectrograph, the cell must necessarily precede the spectrograph. In this case, to use the cell entrance aperture as the spectrograph entrance slit results in the location of sample liquid, of varying refractive index, between the spectrograph slit and the grating. This undesirable situation, which leads to wavelength shifts and absorbance errors, is overcome in the second embodiment of the invention the reverse taper beam cell described below.

The taper beam cell is also useful in an analytical process wherein a sample is caused to fluoresce when exposed to light. Since the excitation light beam does not strike the cell walls, or contaminants on the cell walls, the cell wall will not fluoresce and spurious signals from the cell walls are eliminated. When the samples are analyzed as a function of fluorescence, the cell walls are transparent and the detector is positioned about 90° to the light path passing through the sample.

Figure 4:
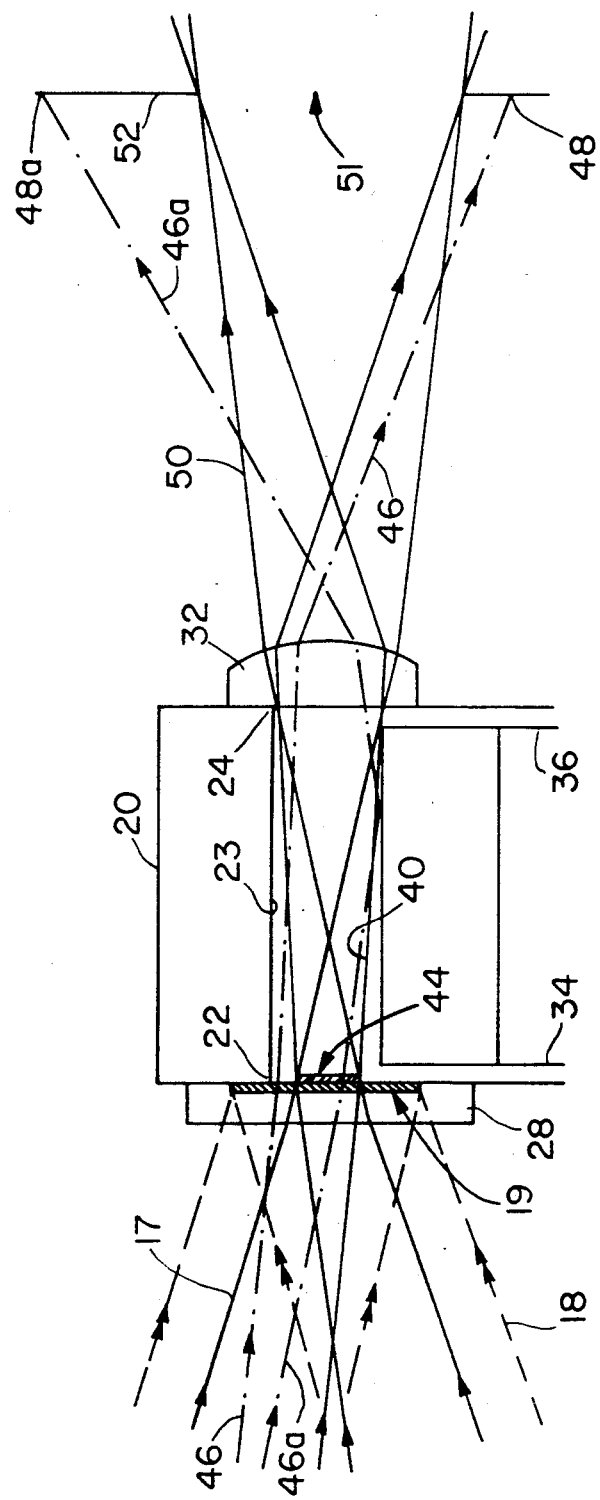
FIG. 4 illustrates the light path through a reverse taper beam cell of this invention.
Figure 5:
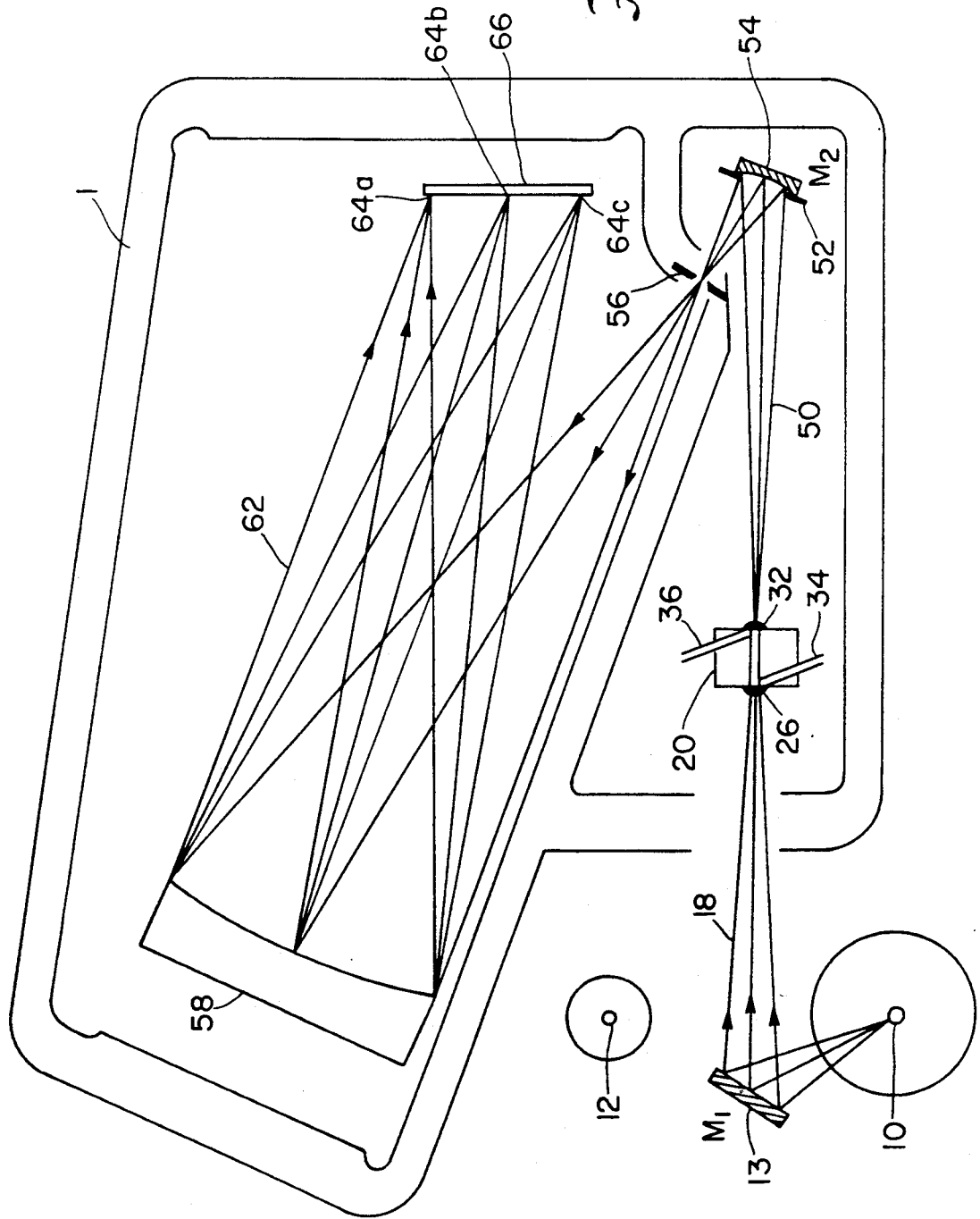
FIG. 5 is a schematic of an apparatus employing the reverse taper beam cell.

In the reverse taper beam cell embodiment, the primary aperture stop of the optical system is the exit of the flow cell bore, and the primary field stop is located after the cell. FIG. 5 discloses a photodiode array-based spectrograph for HPLC using a reverse taper beam cell. The primary field stop is located at mirror M2, which images the exit of the flow cell onto the slit of the spectrograph; the location of which image is unaffected by variations of refractive index in the sample cell. Alternatively, the exit aperture of the cell could be the entrance slit of the spectrograph, with the beam-limiting stop located on the grating. However, utilization of the mirror M2 allows the f/# of the cell to be matched to the f/# of the spectrograph, so optimizing the performance of the instrument. FIG. 4 shows detailed ray paths through the cell. A lens at the cell exit ensures that rays which impinge on the cell walls are blocked from reaching the spectrograph and detector by the field stop near M2. The curvature of the lens is chosen to image a portion of the cell bore near the cell entrance, which is smaller than the cell internal diameter, to fill the field stop near mirror M2. If during the normal course of an HPLC separation, the refractive index in the cell changes, rays inside the cell will bend. However, the design's function is to ensure that rays which pass the two stops, at the cell exit and at M2, will be selected from the essentially uniform light which overfills the entrance of the cell, thus minimizing the effects of refractive index on baseline stability.

Figure 2:
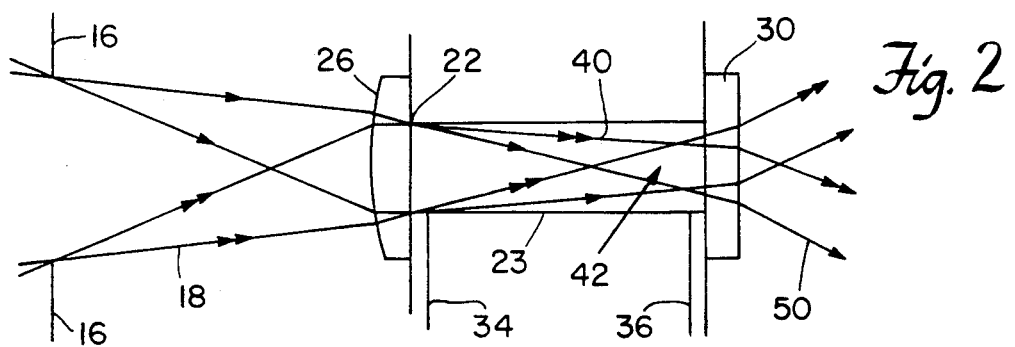
FIG. 2 illustrates the light path for the taper beam cell of this invention.

Referring to FIG. 1, the apparatus is shown which is capable of effecting the taper beam cell of this invention. FIG. 2 shows the details of the light path through the cell. In the apparatus of FIG. 1, a light source 10 emitting electromagnetic radiation over the wavelength range from the ultraviolet to near infrared (for example from at least 190 nm to 800 nm) is provided. A portion of the light emitted by the source 10 passes through aperture 16 to be intercepted by concave holographic grating 14 and dispersed and focussed as light beam 18 onto a plane through the entrance aperture 22 of cell 20. The source 10 has a small emitting area and functions as the entrance slit of the monochromator. Different wave-lengths are focussed at locations such as 19a, 19b and 19c. Rotation of grating 14 illuminates the cell entrance aperture 22 with a selected, approximately single wave-length, e.g., 19b so allowing sample absorbance at that wavelength to be measured. A reference beam and reference detector (not shown in FIG. 1) allow fluctuations in lamp output to be compensated. The focal length of cell entrance lens 26 is chosen to form an image of mask 16 at location 42 in the vicinity of the exit of the cell bore 23. Liquid sample from an HPLC passes through the cell via inlet and outlet ports 34 and 36. As shown in FIG. 2, the envelope 40 of rays traversing the cell bore 23 forms a decreasing taper so that refractive index inhomogeneities, common during gradient elution, may bend the rays, but not so much as to cause them to impinge on the cell internal diameter. The rays exit the cell through window 30, shown here as a plane window, forming a beam 50 which falls entirely within the sensitive area of the photodetector 60. Thus, all rays selected from the source emission by aperture stop 16 and field stop 22 reach the detector without impingement on the cell walls, independently of the sample stream refractive index fluctuations commonly experienced in HPLC.

Figure 3:
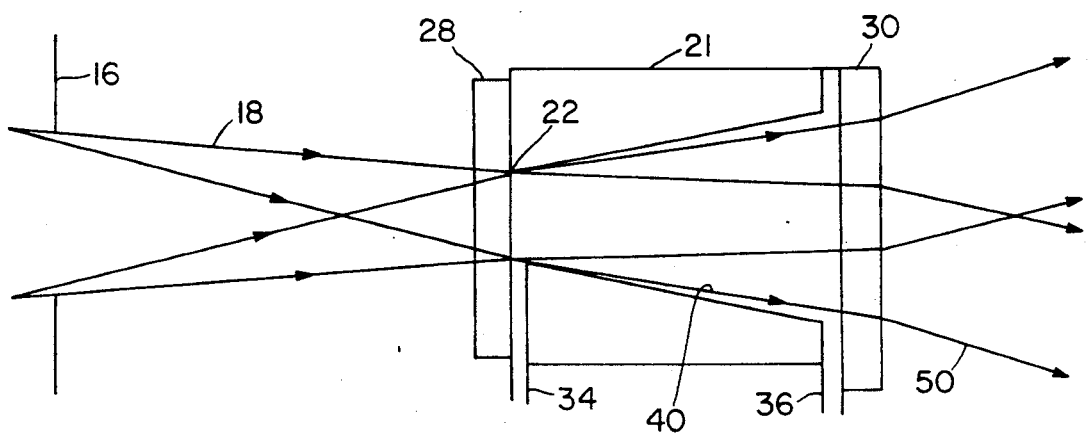
FIG. 3 illustrates the optical path through a prior art taper cell.

Referring to FIG. 3, an example of a prior art cell is shown for comparison. This so-called taper cell 21 (U.S. Pat. No. 4,276,475) achieves the same objective of being insensitive to refractive index fluctuations in the sample cell, but at the expense of substantially increased sample volume, and higher manufacturing costs. A light beam 18 passes through window 28 into cell entrance 22 to form beam envelope 40 which exits through window 30 to form diverging beam 50. The absence of a lens at the cell entrance, allows the beam envelope 40 to diverge through the cell, however, since the cell bore also diverges, the beam envelope 40 does not strike the cell wall.

FIGS. 4 and 5 illustrate the reverse taper beam cell embodiment of this invention, implemented in a photodiode array absorbance detector. Light from either light source 10 or 12, selected to have maximum energy in complementary parts of the spectrum, is directed by rotatable off-axis ellipsoidal mirror 13 to form converging beam 18 and magnified source image 19 which overfills entrance aperture 22 of cell 20.

Lens 32 images cross-section 44 of portion 17 of beam 18, located near cell entrance aperture 22, to fill opening 51 in mask 52. Rays which pass through mask 52 are focussed on slit 56 by concave mirror 54. The demagnification of cell exit aperture 24 at slit 56 by mirror 54 is chosen so that concabe holographic grating 58 is just filled with light. This maximizes the energy through the system at a given spectral resolution. The various wavelengths of diffracted beam 62 are brought to a focus on photodiode array 66 at locations such as 64a, 64b and 64c.

Cross-section 44 of beam portion 17 is smaller than the inside diameter of cell 20. When cell 20 contains a fluid of uniform refractive index, cross-section 44 is advantageously centered on the cell axis. Rays within the envelope of beam 18, such as 46 and 46a, which are not contained within the envelope 40 of rays between cross-section 44 and cell exit aperture 24, are absorbed at 48 and 48a by mask 52 and do not reach photodetector 66. When the refractive index of fluid in the cell changes, as for example during an HPLC gradient separation, rays passing through the cell will bend by refraction and the exact location of cross-section 44 will change, but under normal circumstances will remain within the inside diameter 23 of cell 20. Thus, only rays which stay within envelope 40 contribute to the measured spectrum. Ray envelope 40 is a diverging taper which does not contact the inside surface of the cell, hence the name reverse taper-beam cell.

In FIG. 4, cell entrance window 28 is shown as a plane window. An entrance lens is not essential to the functioning of the reverse taper beam cell invention, although it may improve the performance of the optical system as a whole, by reducing the size of mirror 13, as shown in FIG. 5.

Figure 6:
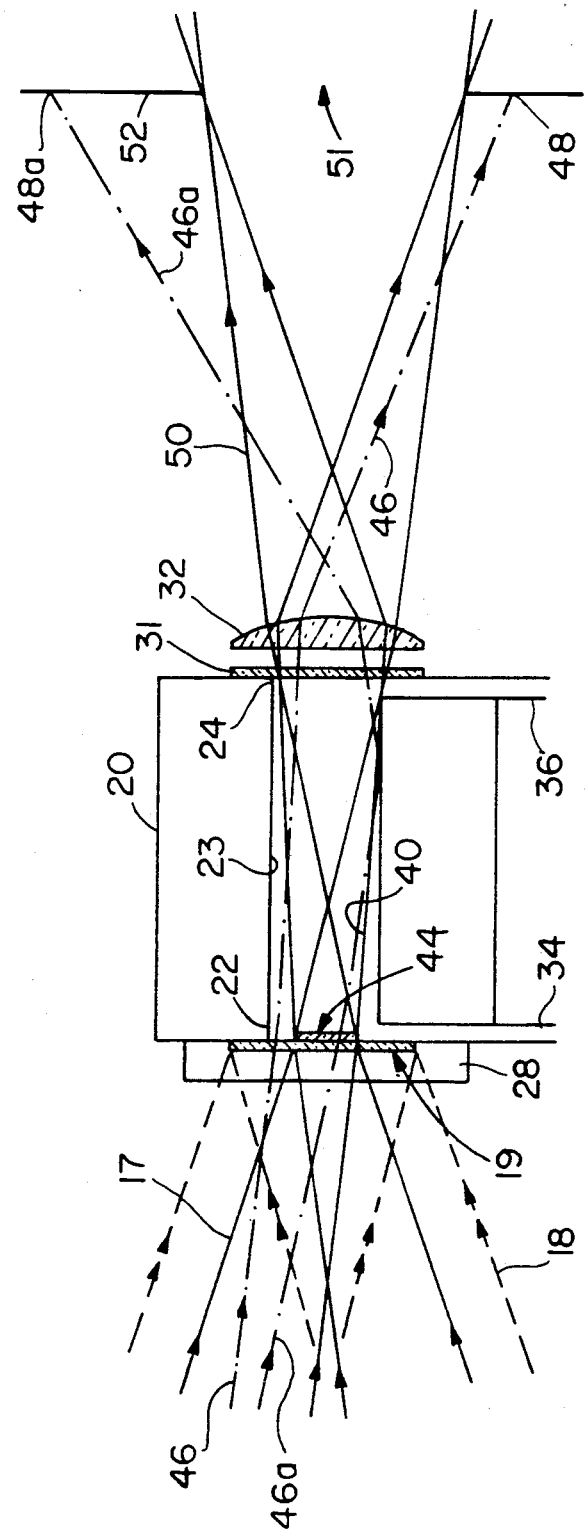
FIG. 6 illustrates the light path through an alternative embodiment of the reverse taper beam cell of this invention.

The reverse taper beam cell of FIG. 6 is the same as the reverse taper beam cell of FIG. 4 except that a plane window 3, is positioned at the cell exit aperture 24 in order to retain liquid within the cell 20 and the lens 32 is not secured to the cell 20. The lens 32 can be positioned at any point between the cell exit aperture 24 and the mask 52 so long as rays within the envelope of beam 18, such as 46 and 46a, which are not contained within the envelope 40 of rays between cross-section 44 and cell exit aperture 24, are absorbed at 48 and 48a by mask 52 and do not reach photodetector 66. Thus the lens 32 need only be positioned after the cell exit operture 24 to perform this function and it need not be secured to the cell 20 at the cell exit aperature 24. Like elements and light rays are identified by the same reference numbers in FIGS. 4 and 6.

Alternative means to lens 32 can be utilized as a focusing means to image cross section 44 of beam 18 to fill opening 51 in mask 82. A representative focussing means comprises a focussing mirror.

What is claimed is:

1. Apparatus for measuring light absorbance in a liquid which comprises:
   a cell of uniform cross-section about a cell axis having a liquid inlet and a liquid outlet,
   a window positioned at a the first axial end of said cell,
   a first focusing means positioned after a second axial end of said cell,
   a light source positioned to direct light along said cell axis through said window, said cell and said first focussing means,
   means to overfill said window with light rays from said source,
   an aperture positioned after said first focusing means,
   said first focusing means having a shape such that light rays which exit said cell and fall within said aperture, have not interacted with walls of said cell and are selected from light rays entering the cell so as to render an absorbance meansurement with said detector insensitive to changes in liquid refractive index.

2. The apparatus of claim 1 wherein said focusing means is a lens.

3. The apparatus of claim 2 wherein said lens is positioned at said second axial end of said cell.

4. The apparatus of claim 1 wherein said detector is a photodiode array.

5. Apparatus for measuring light absorbance in a liquid which comprises,
   a light source positioned to illuminate a cell entrance window with essentially uniformly bright light,
   a cell of uniform cross section about a cell axis having a liquid inlet and a liquid outlet and containing a liquid sample,
   a focusing means positioned after an exit end of said cell,
   an aperture positioned after said focusing means, said focusing means having a shape which ensures that light rays which pass through the aperture have not touched walls of said cell and are selected from said substantially uniformly bright illumination entering said cell and
   means for detecting light exiting said aperture.

* * * * *